(12) United States Patent
Flossmann (10) Patent No.: US 10,507,064 B1
(45) Date of Patent: Dec. 17, 2019

(54) MICROSCOPE TRACKING BASED ON VIDEO ANALYSIS

(71) Applicant: Brainlab AG, Munich (DE)

(72) Inventor: Sven Flossmann, Feldkirchen (DE)

(73) Assignee: BRAINLAB AG, Munich (DE)

( * ) Notice: Subject to any disclaimer, the term of this patent is extended or adjusted under 35 U.S.C. 154(b) by 186 days.

(21) Appl. No.: 15/753,127

(22) PCT Filed: Aug. 24, 2017

(86) PCT No.: PCT/EP2017/071276
§ 371 (c)(1),
(2) Date: Feb. 15, 2018

(87) PCT Pub. No.: WO2018/059837
PCT Pub. Date: Apr. 5, 2018

Related U.S. Application Data

(63) Continuation-in-part of application No. PCT/EP2016/072930, filed on Sep. 27, 2016.

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/25* (2016.02); *A61B 90/37* (2016.02); *G06T 7/277* (2017.01);
(Continued)

(58) Field of Classification Search
CPC ..................................................... A61B 34/20
See application file for complete search history.

(56) References Cited

U.S. PATENT DOCUMENTS 6,434,416 B1 * 8/2002 Mizoguchi ......... G02B 21/0012
600/427
10,092,364 B2 * 10/2018 Schmoll ................. A61B 34/20
(Continued)

FOREIGN PATENT DOCUMENTS

EP 3007635 A1 4/2016
WO WO 2016041051 A1 3/2016

OTHER PUBLICATIONS

International Search Report and Written Opinion, European Patent Office for PCT/2017/071276 dated Nov. 7, 2017.

*Primary Examiner* — Rowina J Cattungal
(74) *Attorney, Agent, or Firm* — Middleton Reutlinger (57) ABSTRACT

The present invention relates to a computer-implemented medical method of determining a spatial position of a medical optical observation device (1), the method comprising executing, on a processor of a computer (2), the steps of:—acquiring position data describing, for a plurality of points in time, the spatial position of the observation device (1) within a co-ordinate system of a medical tracking system (3);—determining, based on the position data, average position data describing an average value for the position of the observation device (1) within the co-ordinate system of the medical tracking system (2);—acquiring image data describing a plurality of images acquired at the plurality of points in time via a camera (4) assigned to the observation device (1) and detecting the field of view (5) of the observation device (1);—determining, based on the image data, optical flow data describing an optical flow for the plurality of images;—determining, based on the average position data and the optical flow data, focal plane position data describing a spatial position of the focal plane (6) of the observation device (1). The present invention further relates to a corresponding computer-program, a corresponding computer
(Continued)

storage medium and a corresponding system for determining the spatial position of a medical optical observation device.

12 Claims, 2 Drawing Sheets

(51) Int. Cl.
    *G06T 7/70*          (2017.01)
    *G06T 7/277*       (2017.01)
    *A61B 90/00*      (2016.01)

(52) U.S. Cl.
    CPC ........ *G06T 7/70* (2017.01); *A61B 2034/2048* (2016.02); *A61B 2034/2051* (2016.02); *A61B 2034/2055* (2016.02); *A61B 2034/2059* (2016.02); *A61B 2034/2063* (2016.02); *A61B 2034/2065* (2016.02); *A61B 2034/2074* (2016.02); *A61B 2090/372* (2016.02); *A61B 2090/373* (2016.02); *A61B 2090/378* (2016.02); *G06T 2207/10056* (2013.01); *G06T 2207/10068* (2013.01); *G06T 2207/30004* (2013.01); *G06T 2207/30244* (2013.01)

(56) References Cited

U.S. PATENT DOCUMENTS

| | | | |
|---|---|---|---|
| 10,383,693 B2 * | 8/2019 | Schmoll | A61B 34/10 |
| 2008/0077158 A1 * | 3/2008 | Haider | A61B 17/15 606/130 |
| 2009/0281419 A1 * | 11/2009 | Troesken | A61B 5/06 600/424 |
| 2014/0316257 A1 | 10/2014 | Woerlein et al. | |

\* cited by examiner

MICROSCOPE TRACKING BASED ON VIDEO ANALYSIS

TECHNICAL FIELD

The present invention relates to the general technical field of determining the position of medical optical observation devices such as medical microscopes during a medical procedure. In particular, the present invention relates to a computer implemented method, a computer program and a system for determining the spatial position of a medical optical observation device.

In medical procedures such as image-guided surgery (IGS), it is desirable to know the precise spatial position (including the spatial location and/or the spatial orientation) of medical instruments and apparatus with respect to each other and with respect to anatomical structures of a patient. In regards to medical optical observation devices such as medical microscopes, it is desirable to know the precise position of the device relative to anatomical structures of a patient observed with the device. For example, medical personnel wishes to associate a visually identified part of the real body with a specific image feature representing that part of the real body in order to eventually determine a location on the specific patient's body part at which a medical procedure is to be carried out.

In a more specific application, knowing the precise spatial relationship between a microscope and the patient allows for:
- visualizing the microscope's focal point on a display of an IGS system with respect to an image representation or images of anatomical structures, for example in axial, sagittal and coronal planes through the anatomy which have been obtained by image modalities like CT or MR;
- superimposing/augmenting the microscope's field of view with images or representations of anatomical structures, either on a separate display or by a semi-transparent projection into the optical path of the microscope.

Known solutions for integrating microscopes into an IGS-environment suggest to calculate the microscope's position exclusively on tracking data, i.e. on data that is obtained by determining the spatial position of one or more tracking markers that are fixedly attached to the microscope. This known approach may lead to wrong results in determining the microscope's position with respect to the patient's anatomy, particularly for the reasons that follow below:

The distance between the microscope focal plane and the microscope's tracking markers is in many cases rather big, in most cases between about 300 to 700 mm, wherein the positional inaccuracies within the focal plane rise with an increased focal length.

Usually, a microscope's field of view is, due to the microscope's magnification factor, rather small, and has for example a diameter between about 20 to 40 mm. Any tracking inaccuracy is therefore even magnified for the viewer.

This may cause the actual position of the focal plane to deviate from the expected position of the focal plane because of slight changes of the microscope position, which lie below the tracking system's detection limit and are therefore not recognized by the tracking system. Registering the field of view as seen through the microscope with supplementary image data may therefore be inaccurate and may lead to an inappropriate augmentation of a user's view through the microscope.

SUMMARY

The present invention provides a precise and reliable method of determining the position of a medical optical observation device in a medical environment, which in turn allows for an accurate augmentation of a user's field of view provided by a medical optical observation device. For reasons of simplicity, the following specification often refers to a microscope. However, it should be noted that the present invention can be applied with any medical optical observation device, including microscopes, endoscopes, exoscopes or head-mounted goggles.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature. A feature for an embodiment which adds an additional function to another embodiment can in particular be added to said other embodiment.

A first aspect of the present invention relates to a computer-implemented medical method of determining a spatial position of a medical optical observation device, the method comprising executing, on a processor of a computer, the steps of:
- acquiring position data describing, for a plurality of points in time, the spatial position of the observation device within a coordinate system of a medical tracking system;
- determining, based on the position data, average position data describing an average value for the position of the observation device within the co-ordinate system of the medical tracking system;
- acquiring image data describing a plurality of images acquired at the plurality of points in time via a camera assigned to the observation device and detecting the field of view of the observation device;
- determining, based on the image data, optical flow data describing an optical flow for the plurality of images;
- determining, based on the average position data and the optical flow data, focal plane position data describing a spatial position of the focal plane of the observation device.

In other words, the present invention suggests to determine the spatial position of focal plane of the observation device not only based on the tracking data obtained from the tracking system that is assigned to the navigation system, but also on data that is obtained from the images provided by an optical camera assigned to the observation device. This camera is adapted to observe the field of view that is provided by the observation device. In this respect, it is important to note that the observation device may be any kind of medical device which receives or transmits electromagnetic radiation, particularly within the visible range of light, and which provides a field of view to a user in a direct or indirect manner. In this context, a direct provision of a field of view means that the user may use the device in the manner of a conventional microscope or magnifying glass, with the device transmitting the electromagnetic radiation to the user's eyes, wherein an indirect provision means that the device transmits data describing the received image to a display unit which in turn displays the corresponding image to the user. In both cases, the image received by the observation device can be "augmented" with further visual data, e.g. a registered image overlay.

According to the present invention, a plurality of (a series of at least two) subsequent images of the field of view of the observation device are taken by the camera, wherein for each image the spatial position of the observation device is determined with the help of the tracking system. Consequently, the spatial position of the observation device is known for each image taken. Further, the spatial position of the focal plane (that includes the focal point at the center) of the observation device can be calculated based on the determined position and the adjusted focal length of the observation device.

In a further step, an average position of the observation device is calculated from the plurality of the determined positions. Additionally, the optical flow of each of the images is determined from which even small positional changes of the observation device can be recognized.

Subsequently, a more accurate spatial position of the focal plane of the observation device can be calculated based on the average position of the observation device and the optical flow of the images.

According to a further embodiment, the spatial position of the observation device itself within the co-ordinate system of the medical tracking unit is finally calculated from the determined spatial position of the focal plane. Since the calculated position of the focal plane is not only based on tracking data but also takes into account an average value for the position of the observation device and the optical flow of the obtained images, the position of the observation device can be determined much more accurately than with known methods that only consider the tracking data obtained from a tracking system.

As already indicated above, the medical optical observation device may be any device which provides a user with an optical image, and which is provided with a camera recording the observation device's field of view. The inventive method may therefore be applied to improve determining the spatial position of any observation device, but may be in particular be used to improve determining the spatial position of a medical microscope, a medical endoscope, a medical exoscope or head-mounted observation goggles. In recent years, such observation goggles are increasingly used in various technical fields, including image guided surgery, particularly in the context of so-called augmented reality. A first kind of such observation goggles comprise miniaturized displays in front of the user's eyes, that can display any kind of information. The goggles are equipped with a position sensor by means of which the spatial orientation of the user's head is determined, and the information displayed in front of the user's eyes can be adapted in accordance with the orientation of the user's head. A second kind of observation goggles differs from the first kind only in that a semi-transparent screen is provided, through which the user can see the surrounding area, but which also serves as a head-up-display in that additional visual information can be projected into the user's field of view.

According to a further embodiment of the present invention, the optical flow is determined for each one of the acquired images, wherein an "average optical flow" is calculated for an image series including each acquired image except for the most recent one. The value for the optical flow of the most recent image is then added to the average value for the optical flow for the set of the preceding images. The spatial position of the focal plane and/or the observation device is then calculated by taking into account this combined value for the optical flow.

The average value for the position of the observation device and/or the average value for the optical flow may be calculated as an arithmetic average value calculated from the underlying individual values. On the other hand, the average value may be a weighted average value calculated from individual values that each have been provided with a weighting factor. In particular, the more recent or later values may be provided with a higher weighting factor than the less recent ones. It is, however, also conceivable that the average value is calculated by applying a Kalman-Filter on the individual values underlying the calculation.

In an even further embodiment, the tracking system for determining the spatial position of the observation device is selected from the group consisting of:
an active or passive optical tracking system, particularly operating within the range of IR-light;
an electromagnetic tracking system comprising at least one field generator and at least one field sensor; and
an ultrasound tracking system comprising at least one ultrasound generator and at least one ultrasound sensor;
a mechanical tracking system comprising at least one joint position sensor configured to detect a relative position between two elements connected to each other via a joint, particularly a ball joint or a rotational joint; and
a tracking system comprising at least one accelerometer and/or at least one gyroscope.

With the spatial position of the focal plane/focal point being determined more accurately, the spatial position of the focal plane/focal point can be displayed on a display in its determined position with respect to anatomical structures of the patient. In a similar manner, the field of view as seen by the observation device can be also displayed on a display device and may further be overlaid with an image and/or a representation of at least one anatomical structure of the patient. Such image can be obtained from any conceivable imaging modality, such as X-ray, CT, MRI or ultrasound modality. Further, an anatomical atlas may provide the display with a registered representation of one or more structures that can be seen in the image provided by the observation device, which may also help in identifying structures which are difficult to identify within the visible range of light. In a quite similar way, an image and/or a representation of at least one anatomical structure of the patient can be registered with the device's field of view, and projected into the optical path of the observation device. By doing so, the user is provided with additional image information when looking through the observation device. In this context, a microscope or head-mounted observation goggles may comprise a head-up-display that provides additional information to the user.

A further aspect of the present invention relates to a program, which, when running on a computer, causes the computer to perform the method steps of a method as described above and/or a computer storage medium on which the program is stored, in particular in a non-transitory form.

DEFINITIONS

The present invention also relates to a system for determining a spatial position of a medical optical observation device, comprising a medical tracking system, a computer on which the above described program is stored and/or run and an optical observation device having a camera that observes the device's field of view.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

Image registration is the process of transforming different sets of data into one co-ordinate system. The data can be multiple photographs and/or data from different sensors, different times or different viewpoints. It is used in computer vision, medical imaging and in compiling and analysing images and data from satellites. Registration is necessary in order to be able to compare or integrate the data obtained from these different measurements.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

The invention also relates to a navigation system for computer-assisted surgery, comprising:

the computer of the preceding claim, for processing the absolute point data and the relative point data;

a detection device for detecting the position of the main and auxiliary points in order to generate the absolute point data and to supply the absolute point data to the computer;

a data interface for receiving the relative point data and for supplying the relative point data to the computer; and a user interface for receiving data from the computer in order to provide information to the user, wherein the received data are generated by the computer on the basis of the results of the processing performed by the computer.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual)

markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

The present invention is also directed to a navigation system for computer-assisted surgery. This navigation system preferably comprises the aforementioned computer for processing the data provided in accordance with the computer implemented method as described in any one of the embodiments described herein. The navigation system preferably comprises a detection device for detecting the position of detection points which represent the main points and auxiliary points, in order to generate detection signals and to supply the generated detection signals to the computer, such that the computer can determine the absolute main point data and absolute auxiliary point data on the basis of the detection signals received. A detection point is for example a point on the surface of the anatomical structure which is detected, for example by a pointer. In this way, the absolute point data can be provided to the computer. The navigation system also preferably comprises a user interface for receiving the calculation results from the computer (for example, the position of the main plane, the position of the auxiliary plane and/or the position of the standard plane). The user interface provides the received data to the user as information. Examples of a user interface include a display device such as a monitor, or a loudspeaker. The user interface can use any kind of indication signal (for example a visual signal, an audio signal and/or a vibration signal). One example of a display device is an augmented reality device (also referred to as augmented reality glasses) which can be used as so-called "goggles" for navigating. A specific example of such augmented reality glasses is Google Glass (a trademark of Google, Inc.). An augmented reality device can be used both to input information into the computer of the navigation system by user interaction and to display information outputted by the computer.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia.

The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumor represents an example of a change in an anatomical structure. If the tumor grows, it may then be said to represent an expanded anatomical structure. This expanded anatomical structure may not be detectable; for example, only a part of the expanded anatomical structure may be detectable. Primary/high-grade brain tumors are for example usually visible on MRI scans when contrast agents are used to infiltrate the tumor. MRI scans represent an example of an imaging method. In the case of MRI scans of such brain tumors, the signal enhancement in the MRI images (due to the contrast agents infiltrating the tumor) is considered to represent the solid tumor mass. Thus, the tumor is detectable and for example discernible in the image generated by the imaging method. In addition to these tumors, referred to as "enhancing" tumors, it is thought that approximately 10% of brain tumors are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimization algorithms are applied in order to find the transformation which results in an optimum degree of similarity. The degree of similarity is preferably measured by way of a measure of similarity (also referred to in the following as a "similarity measure"). The parameters of the optimization algorithm are for example vectors of a deformation field. These vectors are determined by the optimization algorithm in such a way as to result in an optimum degree of similarity. Thus, the optimum degree of similarity represents a condition, for example a constraint, for the optimization algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimizing problem is for example solved iteratively, for example by means of an optimization algorithm which is for example a first-order optimization algorithm, such as a gradient descent algorithm. Other examples of optimization algorithms include optimization algorithms which do not use derivations, such as the downhill simplex algorithm, or algorithms which use higher-order derivatives such as Newton-like algorithms. The optimization algorithm preferably performs a local optimization. If there is a plurality of local optima, global algorithms such as simulated annealing or generic algorithms can be used. In the case of linear optimization problems, the simplex method can for instance be used.

In the steps of the optimization algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighboring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

BRIEF DESCRIPTION OF DRAWINGS

In the following, the invention is described with reference to the enclosed figures which represent preferred embodiments of the invention. The scope of the invention is however not limited to the specific features disclosed in the figures which show.

DETAILED DESCRIPTION

Figure 1:
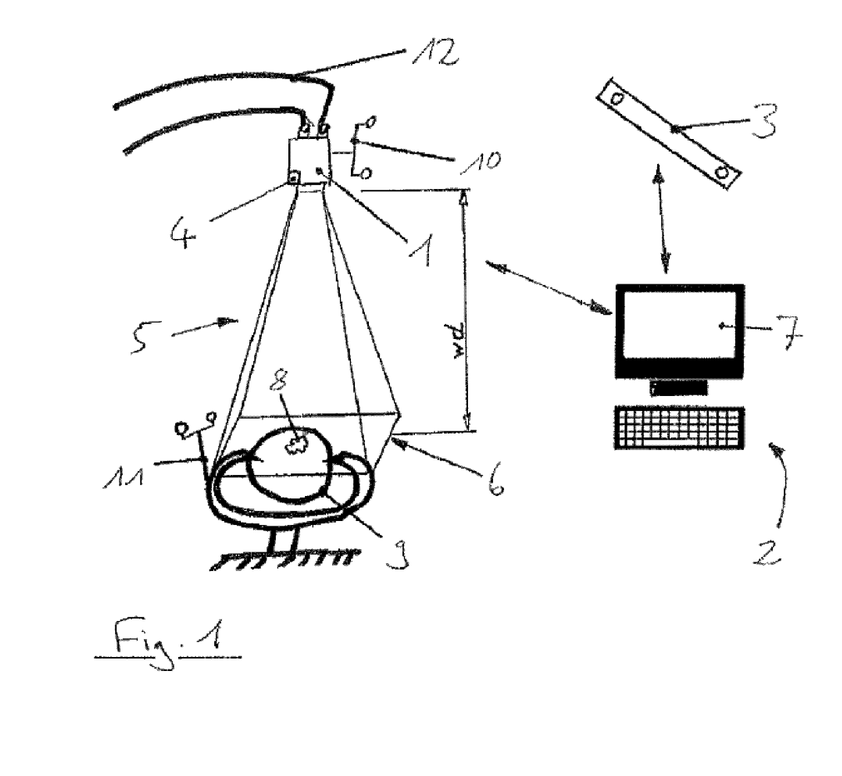
FIG. 1 an IGS-setup according to the present invention, employing a tracked microscope.

FIG. 1 shows an IGS-setup that employs a surgical microscope 1 for obtaining images of a patient, in the shown example a patient's head 9 which contains a specific anatomical structure 8 that is of interest during a surgical procedure. The microscope 1 is mounted on a support arm 12 and is oriented towards the patient 9 in order to have the anatomical structure 8 within the field of view 5 of the microscope 1. For obtaining focused microscope images of the structure 8, the focal distance $w_d$ has to be adjusted such that the structure 8 lies within the focal plane 6.

Further, the microscope 1 comprises an internal optical camera 4 that observes the field of view 5 of the microscope 1 and is adjusted to the focal length $w_d$, as well.

Both, respectively, the microscope 1 and the patient 9 are provided with tracking markers 10 and 11 which can be spatially determined by means of a tracking system (represented by the stereoscopic camera array 3). The positional information provided by the tracking system 3 is processed by a computer 2 thus comprises a display 7 and is connected to the tracking system (as indicated by a first double-arrow in FIG. 1).

For calculating the spatial position of the microscope 1 and/or the spatial position of the focal plane 6, the inventive system does not only consider the obtained positional data of the microscope 1 and the structure 8, but also considers the optical flow of the images provided by camera 4 (which provides computer 2 with camera images and is therefore also connected to computer 2 as indicated by a second double-arrow). In a specific example, the system performs a position-determining method as outlined below:

At first, the spatial position $P_{Mi}$ of the microscope is determined via the tracking system 3 for a plurality of subsequent points in time ($P_{M1}, P_{M2}, \ldots, P_{Mn}$).

Additionally, the optical flow Fi for each image of an image series ($I_1, I_2, \ldots, I_n$) for these points in time is calculated, for example by using the Lucas-Kanade method. As the optical flow usually provides several transformation vectors for different points ($V_{lik}$) in the image, an average over the transformation vectors ($F_i = avg_i(V_{lik})$) is calculated. It is, however, also possible to filter out outlying transformation vectors which may result from movements of objects such as surgical instrument within the image, so as to consolidate different transformation vectors. In case the entire image has moved uniformly, the optical flow is simply calculated from one single transformation vector.

Based on the determined position and on the determined optical flow, the final position of the focus plane $P_{Fn}$ can be calculated as a function of the determined positions and the determined optical flow, for example by the formula $P_{Fn} = P_A + F_A + F_n$), wherein $P_A$ is an average value over the determined positions of the microscope, $F_A$ is an average value over the optical flow determined for the series of all images except for the most recent one, and $F_n$ is the value for the optical flow determined for the most recent image.

Based on the known position of the focus plane $P_{Fn}$, the position of the microscope $P'_{Mn}$ can finally be calculated.

Figure 2:
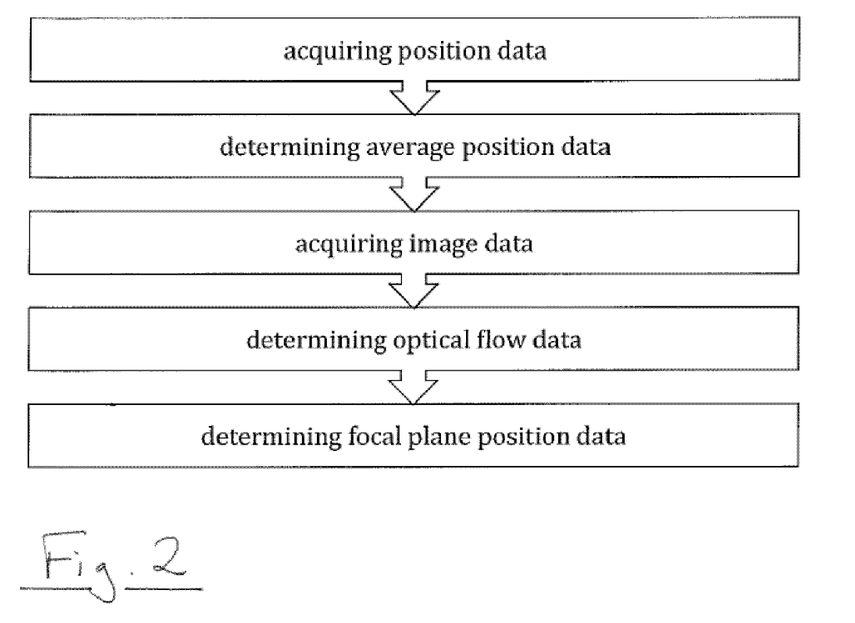
FIG. 2 a method according to the present invention.

FIG. 2 shows the basic steps of the inventive method. Based on acquired position data, average position data is calculated, wherein based on image data, optical flow data is calculated. Based on the calculated average position data and on the calculated optical flow data, focal plane position data is calculated. Based on the focal plane position data, it is further possible to finally calculate the observation device position data.

The invention claimed is:

1. A computer-implemented method of determining a spatial position of a medical optical observation device, the method comprising executing, on at least one processor, the steps of:
    acquiring position data describing, for a plurality of points in time, the spatial position of the observation device within a co-ordinate system of a medical tracking system;
    determining, based on the position data, average position data describing an average value for the position of the observation device within the co-ordinate system of the medical tracking system;
    acquiring image data describing a plurality of images acquired at the plurality of points in time via a camera assigned to the observation device and detecting the field of view of the observation device;
    determining, based on the image data, optical flow data describing an optical flow for the plurality of images;
    determining, based on the average position data and the optical flow data, focal plane position data describing a spatial position of the focal plane of the observation device.

2. The method of claim 1, further comprising the step of:
    determining, based on the focal plane position data, observation device position data describing the spatial position of the observation device within the co-ordinate system of the medical tracking system.

3. The method of claim 1, wherein the observation device is at least one of:
    a medical microscope;

a medical endoscope;

a medical exoscope; and head-mounted observation goggles.

4. The method of claim 1, wherein determining optical flow data involves determining the optical flow for each of the images acquired, wherein a value of the optical flow of the most recent image is added to an average value for the optical flow of the images preceding the most recent image.

5. The method of claim 1, wherein the average value for the position of the observation device is:

an arithmetic average value;

a weighted average value; or an average value obtained from applying a Kalman-filter.

6. The method of claim 1, wherein the average value for the optical flow is:

an arithmetic average value;

a weighted average value; or an average value obtained from applying a Kalman-filter.

7. The method of claim 1, wherein the medical tracking system is at least one of:

an active or passive optical tracking system;

an electromagnetic tracking system including at least one field generator and at least one field sensor; and an ultrasound tracking system including at least one ultrasound generator and at least one ultrasound sensor;

a mechanical tracking system including at least one joint position sensor configured to detect a relative position between two elements connected to each other via a joint, particularly a ball joint or a rotational joint; and a tracking system including at least one accelerometer and/or at least one gyroscope.

8. The method of claim 1, wherein a representation of the focal plane is presented for display on a display device in its determined position with respect to an image and/or a representation of at least one anatomical structure of the patient.

9. The method of claim 1, wherein the field of view of the observation device is presented for display on a display device, being overlaid with an image and/or a representation of at least one anatomical structure of the patient.

10. The method of claim 1, wherein an image and/or a representation of at least one anatomical structure of the patient is projected into the optical path of the observation device.

11. A non-transitory computer readable storage medium storing computing device instructions executable by a processor to perform the steps comprising:

acquiring position data describing, for a plurality of points in time, the spatial position of the observation device within a co-ordinate system of a medical tracking system;

determining, based on the position data, average position data describing an average value for the position of the observation device within the co-ordinate system of the medical tracking system;

acquiring image data describing a plurality of images acquired at the plurality of points in time via a camera assigned to the observation device and detecting the field of view of the observation device;

determining, based on the image data, optical flow data describing an optical flow for the plurality of images;

determining, based on the average position data and the optical flow data, focal plane position data describing a spatial position of the focal plane of the observation device.

12. A system for determining a spatial position of a medical optical observation device, comprising:

a camera, a medical tracking system and a computer having at least one processor, the computer having associated memory and instructions which, when executed by the at least one processor, causes the at least one processor to:

acquire position data describing, for a plurality of points in time, the spatial position of the observation device within a co-ordinate system of a medical tracking system;

determine, based on the position data, average position data describing an average value for the position of the observation device within the co-ordinate system of the medical tracking system;

acquire image data describing a plurality of images acquired at the plurality of points in time via a camera assigned to the observation device and detecting the field of view of the observation device;

determine, based on the image data, optical flow data describing an optical flow for the plurality of images;

determine, based on the average position data and the optical flow data, focal plane position data describing a spatial position of the focal plane of the observation device.

* * * * *